United States Patent [19]

Nowacki et al.

[11] 4,456,016
[45] Jun. 26, 1984

[54] INHALATION VALVE

[75] Inventors: Christopher Nowacki, Arlington Heights; Alfred S. Brisson, Schaumburg, both of Ill.

[73] Assignee: Trutek Research, Inc., Arlington Heights, Ill.

[21] Appl. No.: 394,403

[22] Filed: Jul. 1, 1982

[51] Int. Cl.³ .............................................. A61B 5/08
[52] U.S. Cl. .............................. 128/725; 128/205.23; 128/207.16; 137/103
[58] Field of Search ...................... 128/205.24, 205.23, 128/716, 719, 720, 207.16, 725, 911, 204.23, 204.24; 137/102, 557, 110; 73/861.42, 861.45, 861.47, 861.52, 861.61, 861.65, 861.63

[56] References Cited

U.S. PATENT DOCUMENTS

| | | | |
|---|---|---|---|
| 3,368,555 | 2/1968 | Beasley | 128/204.24 |
| 3,815,593 | 6/1974 | Baumont | 128/204.24 |
| 3,942,547 | 3/1976 | Pfitzner | 128/205.24 |
| 4,141,356 | 2/1979 | Smargassi | 128/204.23 |

*Primary Examiner*—Henry J. Recla
*Assistant Examiner*—Karin M. Reichle
*Attorney, Agent, or Firm*—Trexler, Bushnell & Wolters, Ltd.

[57] ABSTRACT

An inhalation valve is provided for testing the breathing capacity of a person. The valve is constructed of two plastic moldings which snap together and trap a flexible elastomeric valve diaphragm between them. The valve is provided with a mouthpipe. Exhalation through the mouthpipe deflects the diaphragm to permit substantially unrestricted exhalation. Inhalation is through a laterally displaced passageway having a transverse wall therein to produce a pressure drop. Tubular fittings are provided in the pressure drop area behind the wall and exteriorally of the flow path to provide an input to an electronic apparatus to indicate the efficiency of breathing.

12 Claims, 5 Drawing Figures

INHALATION VALVE

BACKGROUND OF THE INVENTION

In the treatment of patients suffering from various respiratory problems, either of acute or chronic nature, involving the lungs, bronchia, etc., it is often necessary to test the breathing capacity of the patient. Prior art devices or apparatus for this purpose have tended to be either quite expensive or of a low degree of accuracy.

OBJECTS AND SUMMARY OF THE PRESENT INVENTION

It is an object of the present invention to provide an inhalation valve having a portion to be placed in a patient's mouth while the patient inhales and exhales, which valve is of economical and rugged construction and develops a pressure differential signal for handling by electronic apparatus to provide a measure of the patient's breathing capacity.

It is a more specific object of the present invention to provide such an inhalation valve which is of essentially two-piece molded plastic construction, with a diaphragm valve or flap trapped between the two pieces upon assembly thereof.

Yet another object of the present invention is to provide an inhalation valve having structure therein for developing a pressure differential signal to be coordinated with electronic apparatus to measure the breathing capacity of a patient.

In achieving the foregoing and other objects of the present invention, an entry portion of an inhalation valve comprises a single piece molded of plastic and including a restricted passageway having a barrier therein which produces a reduced air pressure behind the barrier as compared with ambient pressure. An air pressure connection is provided from behind the barrier, and another such connection is provided exteriorally of the restricted flow passage to provide a pressure differential which is applied to an electronic apparatus as disclosed in our copending application Ser. No. 415,735, filed Sept. 7, 1982, and entitled "Inhalation Transducer Circuit". A second exit or mouthpiece portion is a single molded plastic element forming a snap-together fit with the first-mentioned portion, trapping a diaphragm or flap valve between the two pieces. The second piece includes a mouth pipe to be held by the patient in his mouth while breathing in and out. Upon inhalation incoming air passes through a restricted flow path to develop a pressure differential, but on exhalation the diaphragm of flap valve opens to provide an essentially unrestricted exit path for exhalation.

THE DRAWINGS

The present invention will be best understood with reference to the following specification taken in connection with the accompanying drawings wherein.

DETAILED DESCRIPTION OF THE ILLUSTRATED EMBODIMENT

Figure 2:
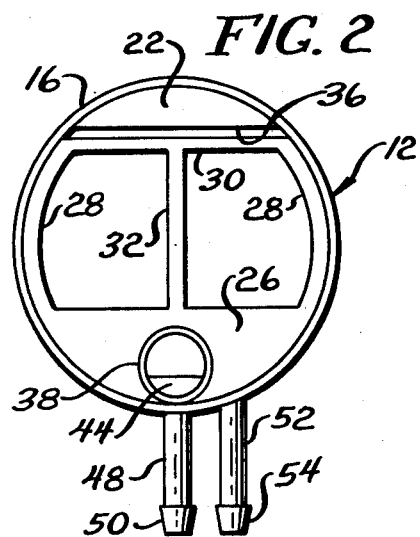
FIG. 2 is an end view of the first or entering piece of the valve as taken from the left end of FIG. 1.
Figure 3:
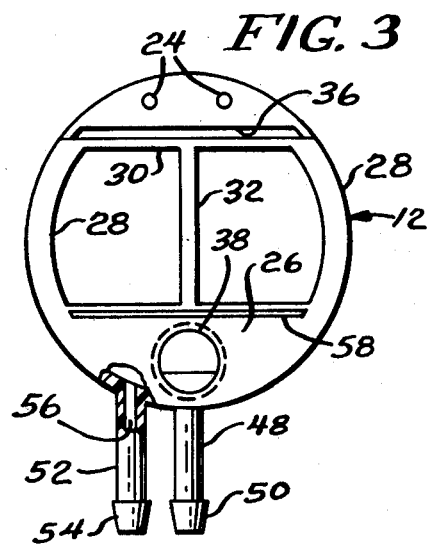
FIG. 3 is an end view of the first or entering piece of the valve as taken from the right end of FIG. 1.
Figure 4:
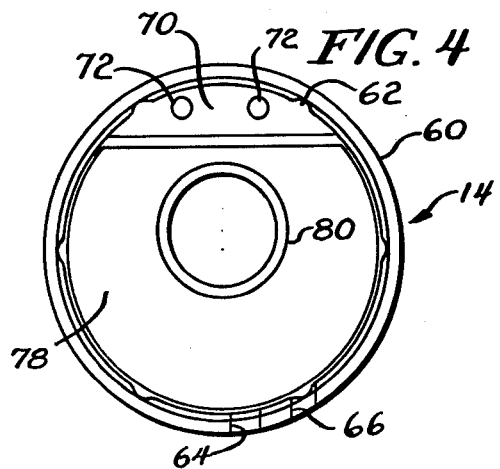
FIG. 4 is an end view of the second or mouthpiece portion of the valve as taken from the left end in FIG. 1.
Figure 5:
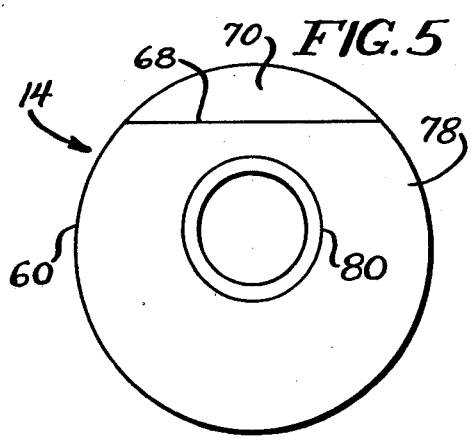
FIG. 5 is an end view of the second or mouthpiece portion of the valve as taken from the right end in FIG. 1.

Referring now in greater detail to the drawings there is shown in inhalation valve 10 of generally two piece construction of molded plastic, including a first or front portion 12 and an exit or mouthpiece portion 14. The first or front portion 12 is seen in FIGS. 2 and 3 and includes an outer, generally cylindrical shell 16. The outer surface of the shell 16 tapers outwardly at 18 from the rear or inner edge of the shell and is provided with a shoulder 20 cooperable with a mouthpiece 14 to lock the two parts together, as will be brought out hereinafter. The upper portion of the shell 16 is provided with a depending wall 22 in the form of a circular segment, and two integral, axially extending pins 24 are provided on the back of the wall 22.

The shell 16 at the bottom thereof is provided with an upstanding wall 26, also in the form of a circular segment, but of greater radial extent than the wall 22. The wall 26 is spaced rearwardly or inwardly (to the right in FIG. 1) of the wall 22, and has upstanding therefrom circular arcs 28 supporting a transverse bar 30 lying on a circular chord. A diametral rib 32 extends between the bar 30 and the wall 26.

An elastomeric diaphragm or valve flap 34 is supported by the pin 24 and in inactive position lies in a vertical plane, with the wall 26 on the front side thereof, and with the wall 26, arcs 28, bar 30, and rib 32 lying behind the valve flap. There is a vertical space 36 between the top of the bar 30 and the bottom of the wall 22 to provide clearance for the diaphragm 34.

A relatively small conduit or pipe 38 lying tangent to the inner surface of the shell 16 is provided at the bottom of the inlet portion 12, having an entering end 40 spaced inwardly of the entering end 42 of the shell 16. The rear end of the pipe 38 exits through the wall 26. Relatively near the front or inlet end of the pipe 38 there is provided a partial, upstanding wall 44 equal in height to roughly one-third the diameter of the pipe 38. Slightly to the rear of this wall there is provided a radial, downwardly directed bore 46 continued through a tubular fitting 48 having an enlargement 50 at the end thereof for receipt of a connecting tubing of rubber or plastic. A similar fitting 52 having a connecting end 54 is spaced to one side of the fitting 48 and is provided with an axial bore 56 opening interiorally of the shell 16, but exteriorally of the pipe 38.

The first portion of the valve further includes an axially extending wall 58 protruding from the rear of the circular segment wall 26 in cantilever fashion.

The second or rear portion 14 of the valve includes a generally cylindrical outer wall 60, the forward portion of which encircles the shell 38 of the first portion. And inwardly protruding, interrupted flange or rib 62 in the cylindrical wall is spaced slightly from the entering end thereof, and snaps over the shoulder 20 of the first portion to hold the two portions in assembled relation. The flange or rib is rounded in section to facilitate camming over other parts, while the interruption of the flange or rib inhances resiliency thereof, facilitating withdrawal from a mold and snapping together of the two portions of the valve. The forward portion of the cylindrical wall is provided with two slots 64, 66 to accommodate the pneumatic tubes 48 and 52.

The upper portion of the cylindrical wall 60 is cut off by a chordal wall 68 remote from the front portion of the wall 60, in the top area thereof, and is joined to the top of the cylindrical wall by a segmental wall 70. The segmental wall is provided with a pair of recesses 72 which receive the pins 24. The inner section of the chordal wall 68 and the segmental wall 70 is recessed at 74 to accommodate the cross bar 30 of the first portion of the valve. Below the chordal wall 68 the cylindrical wall 60 is recessed to provide a shoulder or stop 76 for the cylindrical shell 16 of the first portion 12.

The rear of the cylindrical wall 60 is terminated by a transverse wall 78 which is penetrated by a mouthpipe 80 which extends into the space interiorly of the cylindrical wall 60 to a position with the end 82 thereof overlapping the wall 58 with the two portions of the valve in assembled relation. The mouthpipe 80 also extends a considerable distance rearwardly of the transverse wall 78 at 84 for insertion in the mouth of a patient.

Figure 1:
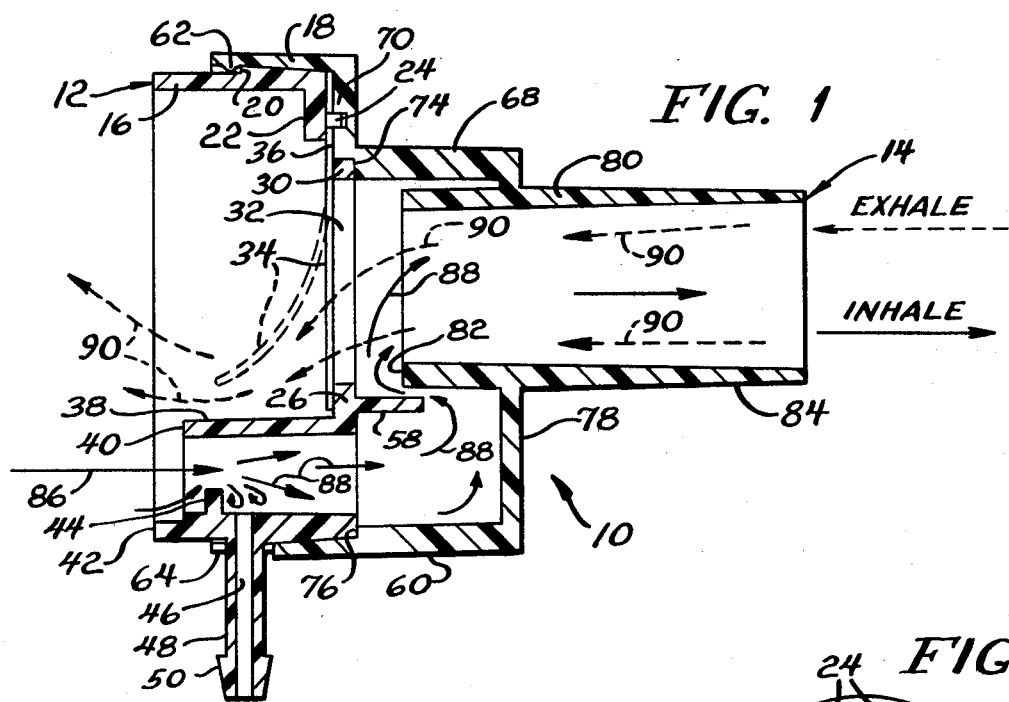
FIG. 1 is an axial sectional view through the inhalation valve forming the subject matter of the present invention.

The first and second portions of the inhalation valve 10 snap together as shown in FIG. 1 to form a valve body, trapping the diaphragm or valve flap 34 in position, suspended and positioned by the pins 24. Upon inhalation the diaphragm is pulled against the rib 32, the segmental wall 26, and the arcuate members 28 so that air cannot pass directly from the front the valve to the mouthpipe. The air passes into the tube or cylinder 38 as indicated by the arrow 86, and continues along the path indicated by the succession of arrows 88 into the mouthpipe 80. A pressure drop is caused by the wall 44, and thus the pressure at the entrance to the passageway 46 is less than it is at the entrance passageway 56. Therefore, there is a pressure differential that can be measured, as by tubing connected to the two fittings 48 and 52 and to a suitable electronic apparatus as noted heretofore, and this pressure differential is an indication of the force or efficiency with which the patient inhales.

Upon exhalation the diaphragm 34 simply flexes to the left in FIG. 1 as shown in broken lines, whereby exhaled air exits along the broken line arrows 90 with substantially no restriction to exhalation.

Alignment of the mouthpipe with the opening covered by the diaphragm, coupled with the restricted inhalation passageway into the mouthpipe, leads to 100% of the exhaled air passing directly out past the deflected diaphragm. This prevents any false reading being generated on exhalation.

It will now be seen that we have disclosed a remarkably simple and inexpensive inhalation valve which comprises only two molded plastic parts which snap together with a flexible elastomeric diaphragm between them. The plastic material makes the valve remarkably easy to clean, but the construction is so inexpensive that a valve can be assigned to a single patient, and subsequently discarded if desired.

Spacing of the entering end 40 of the pipe 38 in from the entering end 42 of the body is important in that if a patient should cover the entering end of the body, as with the palm of his hand, there will be no pressure differential, and hence no electric signal transduced. This prevents a false reading The specific example of the invention as herein shown and described is for illustrative purposes only. Various changes will no doubt occur to those skilled in the art, and will be understood as forming a part of the present invention insofar as they fall within the spirit and scope of the appended claims.

The invention is claimed as follows:

1. An inhalation valve comprising a body, a mouthpipe for insertion in a person's mouth, said mouthpipe being connected to said body and having an air passageway therethrough, said body having an exhalation air passageway therethrough in substantial alignment with said mouthpipe air passageway, diaphragm valve means disposed in said body between and in substantial alignment with said passageways said diaphragm valve means deflecting for permitting free, straight-through exhalation from said mouthpipe through said exhalation passageway but closing for preventing straight-through inhalation therethrough, means in said body providing an inhalation air passageway substantially parallel to and displaced laterally of said mouthpipe air passageway and in air flow communication therewith, said inhalation air passageway communicating with said mouthpipe air passageway such that no exhalation air will flow thereinto, both said exhalation air passageway and said inhalation air passageway being open to atmosphere at a common end opposite to said mouthpipe, said inhalation air passageway having a restriction therein, and means providing a pneumatic connection downstream of said restriction in the direction of inhalation air flow for measuring a function of the pressure drop produced at said restriction.

2. A valve as set forth in claim 1 and including means providing a second pneumatic connection into said body independent of said inhalation air passageway for measuring differential pressure.

3. A valve as set forth in claim 1 wherein said restriction comprises a transverse wall extending part way across said inhalation air passageway from only one side thereof.

4. A valve as set forth in claim 1 wherein said body comprises two portions, said diaphragm valve means having an upper edge secured between said two portions.

5. A valve as set forth in claim 4 wherein said two portions are secured together by snap-together retaining means.

6. A valve as set forth in claim 5 and further including locating pin means extending between said two portions and through said diaphragm valve means.

7. A valve as set forth in claim 1 wherein the air flow communication from said inhalation air passageway to said mouthpipe passageway comprises means for providing a reentrant flow path to inhibit reverse air flow through said inhalation air passageway upon exhalation.

8. An inhalation valve comprising a body having a generally cylindrical front portion having a front end and a rear end and a generally cylindrical rear portion having a front end and a rear end said front end of said front portion being open to atmosphere said rear end of said rear portion, having a transverse wall, a mouthpipe extending through said transverse wall and having a rearwardly extending portion for insertion in a person's mouth and a forwardly extending portion including a front end extending toward the front portion of said body, said mouthpipe having an air passageway therethrough, diaphragm valve means disposed transversely between the rear end of said front portion and the front end of said rear portion and deflecting for permitting free straight-through exhalation through said mouthpipe passageway and said front portion to atmosphere but closing for preventing straight-through inhalation therethrough, said diaphragm valve means being spaced from the front end of said mouthpipe, wall means in said front and rear portions providing an inhalation air passageway communicating with atmosphere at the front end of said front portion and displaced laterally of said mouthpipe air passageway said wall means defining in said rear portion rearwardly of the front end of said mouthpipe a reentrant air passageway between said inhalation air passageway and said mouthpipe air passageway said reentrant air passageway communicating with said mouthpipe air passageway such that no exhalation air flows thereinto, first air pressure sensing means comprising a restriction in said inhalation air passageway for producing a pressure drop thereacross upon passage of air therethrough air, and means adjacent said restriction on the downstream side thereof for providing an indication of a function of the pressure drop produced at said restriction.

9. A valve as set forth in claim 8 wherein said front portion and said rear portion comprise two separate molded plastic parts, said mouthpipe being integral with said rear portion and said inhalation air passageway being integral with said front portion, and rear portion, said front and rear portions including integral means for snapping together to hold said body portions together with said diaphragm valve means in part trapped therebetween.

10. A valve as set forth in claim 9 wherein said front portion and said rear portion respectively have mutually confronting walls having cooperating pin and hole means with said pin means passing through a portion of said diaphragm valve means.

11. A valve as set forth in claim 8 wherein the means adjacent the restriction in the inhalation air passage is exposed to reduced air pressure caused by pressure drop across said restriction, and further including a second air pressure sensing means in said first body portion and outside of said inhalation air passage for providing in cooperation with said first air pressure sensing means a measure of pressure differential.

12. A valve as set forth in claim 8 wherein the rear portion of said generally cylindrical front portion has an edge and wherein the wall means providing the inhalation air passageway has an entering end spaced from the edge of the rear portion of said cylindrical front portion in the direction of inhaled air.

* * * * *